United States Patent

Radley et al.

(10) Patent No.: US 9,423,363 B2
(45) Date of Patent: Aug. 23, 2016

(54) OBJECT MONITORING USING MULTI SPECTRAL RADIATION

(75) Inventors: Ian Radley, Durham (GB); Ben Cantwell, Durham (GB); David Edward Joyce, Durham (GB); Paul Scott, Durham (GB)

(73) Assignee: Kromek Limited, Sedgefield (GB)

( * ) Notice: Subject to any disclaimer, the term of this patent is extended or adjusted under 35 U.S.C. 154(b) by 234 days.

(21) Appl. No.: 14/236,408

(22) PCT Filed: Aug. 1, 2012

(86) PCT No.: PCT/GB2012/051864
§ 371 (c)(1),
(2), (4) Date: Mar. 25, 2014

(87) PCT Pub. No.: WO2013/017878
PCT Pub. Date: Feb. 7, 2013

(65) Prior Publication Data
US 2014/0219419 A1    Aug. 7, 2014

(30) Foreign Application Priority Data

Aug. 1, 2011  (GB) .................................. 1113219.8
Aug. 1, 2011  (GB) .................................. 1113222.2
Aug. 1, 2011  (GB) .................................. 1113224.8

(51) Int. Cl.
*G01N 23/087*   (2006.01)
*G01N 23/04*    (2006.01)
*G01V 5/00*     (2006.01)

(52) U.S. Cl.
CPC .............. *G01N 23/087* (2013.01); *G01N 23/04* (2013.01); *G01V 5/0041* (2013.01); *G01N 2223/423* (2013.01)

(58) Field of Classification Search
CPC .................................................. G01N 23/087
See application file for complete search history.

(56) References Cited

U.S. PATENT DOCUMENTS 4,613,754 A    9/1986   Vinegar et al.
5,600,303 A    2/1997   Husseiny et al.
(Continued)

FOREIGN PATENT DOCUMENTS

EP    2377467 A1    10/2011
EP    2405260 A1    1/2012
(Continued)

OTHER PUBLICATIONS

Dedman, Emma, "International Search Report," prepared for PCT/GB2012/051864, as mailed Jan. 11, 2013, 4 pages.
(Continued)

*Primary Examiner* — Hoon Song
(74) *Attorney, Agent, or Firm* — Winstead PC

(57) ABSTRACT

A method for monitoring objects for example for facilitating the identification and/or authentication of objects comprises: in a first recording phase: irradiating an object with a suitable source of radiation, collecting intensity information about radiation emergent from the object, resolving the intensity information spectroscopically between at least two energy bands, and storing the resultant dataset as a reference dataset; and in a second verification phase: irradiating an object with a suitable source of radiation, collecting intensity information about radiation emergent from the object, resolving the intensity information spectroscopically between at least two energy bands, and using the resultant dataset as a test dataset; identifying the object and retrieving its corresponding reference dataset; comparing the test dataset and the reference dataset within predetermined tolerance limits, and: in the event that the reference dataset and the test dataset correspond within the predetermined tolerance limits, treating the object as verified or in the event that the reference dataset and the test dataset differ by more than the predetermined tolerance limits, in a third identification phase: numerically processing the resolved intensity information from the test dataset to derive therefrom a dataset of information characteristic of the composition of the object, and using this information to identify the composition of the object.

18 Claims, 1 Drawing Sheet

(56) References Cited

U.S. PATENT DOCUMENTS

| | | | |
|---|---|---|---|
| 6,018,562 A | 1/2000 | Willson | |
| 2006/0233302 A1 | 10/2006 | Might et al. | |
| 2007/0030953 A1* | 2/2007 | Sommer, Jr. | G01N 23/06 378/53 |
| 2007/0263769 A1* | 11/2007 | Roell | A61N 5/103 378/65 |
| 2009/0086907 A1 | 4/2009 | Smith | |
| 2010/0002834 A1 | 1/2010 | Gudmundson et al. | |
| 2010/0172470 A1 | 7/2010 | Kuwabara | |
| 2010/0303287 A1 | 12/2010 | Morton | |
| 2011/0075800 A1 | 3/2011 | Bjorkholm | |
| 2014/0226788 A1 | 8/2014 | Radley et al. | |
| 2014/0297228 A1 | 10/2014 | Radley et al. | |

FOREIGN PATENT DOCUMENTS

| | | |
|---|---|---|
| GB | 2441551 A | 3/2008 |
| GB | 2454782 A | 5/2009 |
| JP | H06205767 A | 7/1994 |
| JP | 2009092658 A | 4/2009 |
| JP | 4614001 B2 | 1/2011 |
| WO | WO-2008034232 A1 | 3/2008 |
| WO | WO-2008040119 A1 | 4/2008 |
| WO | WO-2009046529 A1 | 4/2009 |
| WO | WO-2010086636 A2 | 8/2010 |

OTHER PUBLICATIONS

Midgley, S. M., "Materials Analysis Using X-Ray Linear Attenuation Coefficient Measurements at Four Photon Energies," Phys. Med. Biol. 50 (2005), pp. 4139-4157.

Midgley, S. M., "A Parameterization Scheme for the X-Ray Linear Attenuation Coefficient and Energy Absorption Coefficient," Phys. Med. Biol. 49 (2004), pp. 307-325.

Midgley, S.M., "Measurements of the X-ray linear attenuation coefficient for low atomic number materials at energies 32-66 and 140keV", Radiation Physics and Chemistry, Elsevier Science Publishers BV, Amsterdam NL, vol. 72, No. 4, Mar. 1, 2005, pp. 525-535.

Okunade, A.A., "Parameters and computer software for the evaluation of mass attenuation and mass energy-absorption coefficients for body tissues and substitutes", Journal of Medical Physics, vol. 32, No. 3, 2007, pp. 124-132.

Kerur, B.R., et al., "Mass attenuation coefficient of saccharides for X-rays in the energy range from 8keV to 32keV", Radiation Measurements, Elsevier, Amsterdam, NL, vol. 44, No. 1, Jan. 1, 2009, pp. 63-67.

Han, I., et al., "Mass Attenuation coefficients, effective atomic and electron numbers of Ti and Ni alloys", Radiation Measurements, Elsevier, Amsterdam, NL, vol. 44, No. 3, Mar. 1, 2009, pp. 289-294.

Dedman, Emma, "International Search Report" for PCT/GB2012/051865, as mailed Jan. 17, 2013, 6 pages.

Jackson, Daphne F. et al., "X-ray Attenuation Coefficients of Elements and Mixtures", Physics Reports (Review Section of Physics Letters) 70, No. 3, 1981, pp. 171-233.

Kaneyasu, Tatsuo et al., "Dual-Energy X-ray CT by Compton Scattering Hard X-ray Source", Proceedings of 2005 Particle Accelerator Conference, IEEE, 2005, pp. 1291-1293.

Dedman, Emma, "International Search Report," prepared for PCT/GB2012/051863, as mailed Dec. 21, 2012, 4 pages.

* cited by examiner

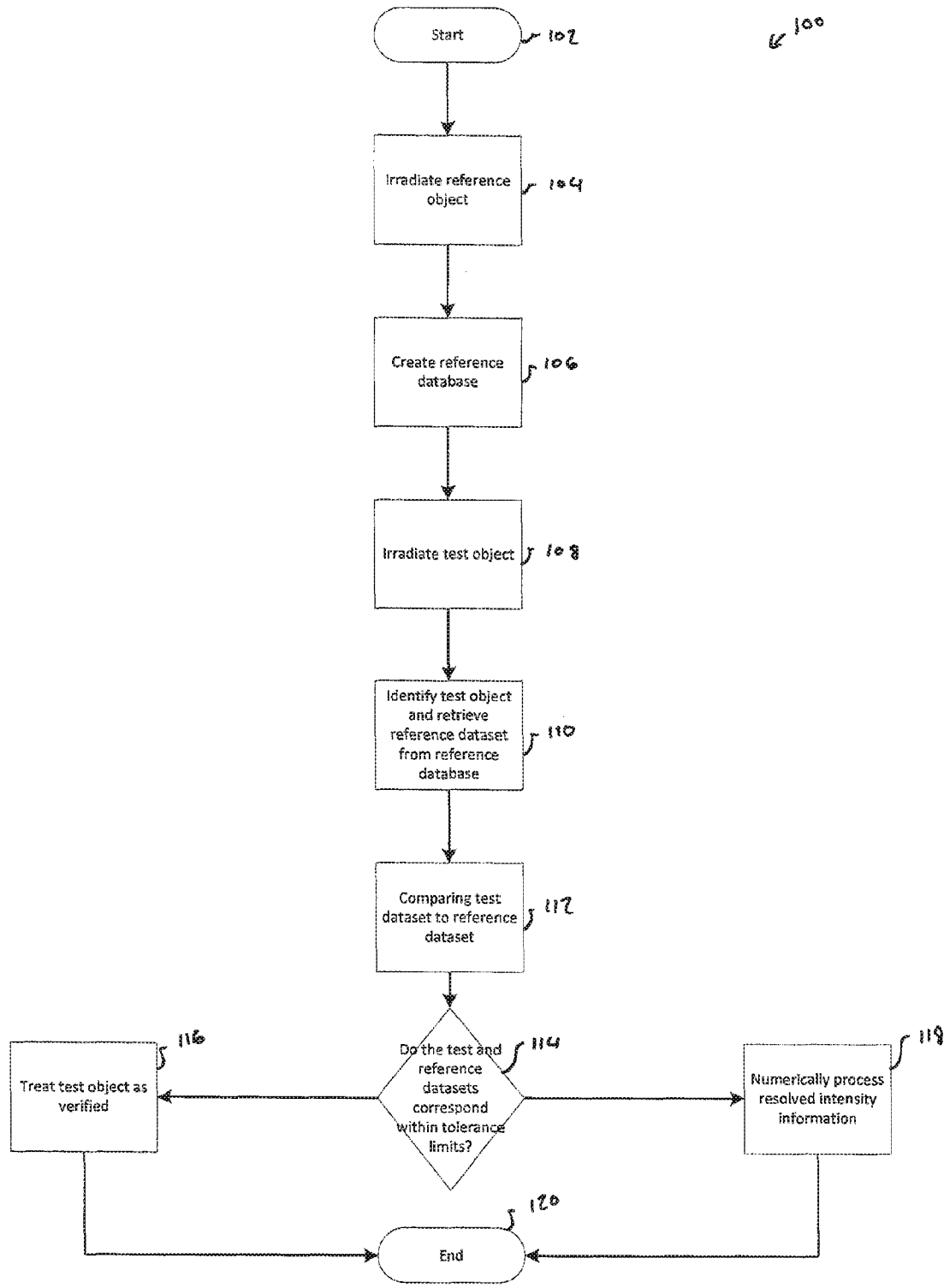

OBJECT MONITORING USING MULTI SPECTRAL RADIATION

FIELD OF THE INVENTION

This invention relates to a method of monitoring objects by radiological examination in particular using X-rays, and to a method of processing of detected radiation data from such a radiological examination. This invention relates in particular to the monitoring of condition and/or composition changes in a test object by comparison to reference data.

This invention relates in particular to the creation of a set of compound-specific parameters, including in certain embodiments data representative of mass thickness, and including in certain embodiments data representative of multiple orders of weighted atomic number which we call herein a Compound Proton Number Set. In their infinite form such numbers identify and depend upon the composition of a compound. The invention in a particular embodiment includes a method for calculating a number and preferably a high number of dimensions of the Compound Proton Number Set using X-ray measurements measured at multiple energies, as a method for material identification.

The invention may in particular facilitate the detection of the presence of and/or classification or identification of particular target materials within a test object, for example materials which might represent a threat to security, a breach of customs regulations or the like. The invention in particular relates to baggage screening and other security, industrial and medical applications where the detection and identification of foreign objects in an image is of benefit. However the invention is not limited to the investigation of objects inside other objects. Materials ID of stand-alone objects is also useful.

The invention may in particular relate to a method and apparatus making us of a semiconductor detector device comprising a large direct band gap semiconductor material, for example a group II-VI semiconductor material such as cadmium telluride (CdTe), cadmium zinc telluride (CZT), cadmium manganese telluride (CMT) or the like, for example formed as a bulk single crystal but is not limited to any particular class of detectors.

BACKGROUND

It is desirable to scan the contents of objects at security and customs checkpoints to gain information about content, for example to obtain an indication that the contents of the object do not constitute a threat to security or a breach of customs regulations. It is also desirable to scan the contents of objects for other purposes such as quality control, content verification, degradation monitoring etc.

It is known that information useful in this regard may be obtained from a spectroscopic analysis of radiation received at a detector after interaction with an object under test for example by scanning the object from a suitable high energy electromagnetic radiation source, collecting emergent radiation at a suitable detector after interaction with the object, and processing the emergent radiation spectroscopically, for example against reference data, to draw conclusions about the composition of the object.

The Beer-Lambert law states that for a beam of photons of energy E with intensity $I_0$ incident on a material with thickness, t (cm), the intensity that emerges is $$I = I_0 e^{-\mu t} \quad 1$$

where $\mu$ is the linear attenuation coefficient and is defined as the probability of interaction per unit distance travelled. This has units of $cm^{-1}$. It is often preferable to work with a mass attenuation coefficient which is the linear attenuation coefficient ($\mu$) divided by the material density ($\rho$). The mass attenuation coefficient $$\left(\frac{\mu}{\rho}\right)$$

therefore has the units $g^{-1}cm^2$. The mass attenuation coefficient, in X-ray physics is also generally denoted by the symbol $\alpha$, not to be confused with the fine structure constant which also shares this symbol. As used herein $\alpha$ refers to the mass attenuation coefficient, unless otherwise specified. Therefore the Beer-Lambert law expressed in terms of the mass attenuation coefficient is $$I = I_0 e^{-\frac{\mu}{\rho}(\rho t)} = I_0 e^{-\alpha(\rho t)} \quad 2$$

where the product of the density and the distance ($\rho t$) is defined as the mass thickness, x.

X-rays interact with the matter in a number of ways, which may lead to attenuation of the beam. The three most important methods of interaction are;

Compton Scattering

Photoelectric Effect

Pair production

Other effects, such as Thompson Scattering, play a smaller role, but which process dominates depends upon the mass absorption characteristics of the medium, which is in turn dependent upon the energy of the photons.

Which of these processes dominates is dependent on the mass absorption characteristics of the target (directly related to the atomic number, Z) and the energy of the X-ray.

At low energies the Photoelectric Effect tends to dominate the linear absorption coefficient ($\mu_\lambda$), as the photon energy increases the Compton Effect starts to dominate, until Pair Production occurs and dominates at energy above 1022 keV. As X-ray applications generally use X-ray up to several hundred keV, Pair Production does not occur and the attenuation of the beam is mainly caused by a combination of the other two effects.

Several attempts have been made to accurately describe the attenuation from an element, but all are approximations to real data which make a number of assumptions. One of the most widely accepted texts by Jackson and Hawkes, (DF Jackson and DJ Hawkes, X-ray attenuation coefficients of elements and mixtures; Physics Reports 70 (3) pp 169-233 (1981)), present a method for estimating the linear attenuation coefficient as $$\mu(Z, E) \cong \rho \frac{N_A}{A} Z \quad 3$$
$$\left\{ 4\sqrt{2} Z^4 \alpha^4 + \left(\frac{mc^2}{E}\right) \phi_0 \sum_{nll'} f_{nll'} + \sigma_{KN} + \frac{Z(1 - Z^{b-1})}{Z'^2} \sigma_{SC}^{coh}(Z', E') \right\}$$

where $\rho$ is the mass density, $N_A$ is Avagadro's number, A is the atomic mass, Z the atomic number, $\alpha$ in this case is the fine structure constant, m the electron rest mass, c the speed of light, $\phi_0$ is the Thomson classical cross section per atom, $f_{nll'}$ is a collection of terms for the Photoelectric cross section, $\sigma_{KN}$ is the Compton cross section and $\sigma_{sc}^{coh}$ is the Rayleigh scattering cross section of a standard element Z' at energy $$E' = \left(\frac{Z'}{Z}\right)^{1/3} E.$$

The fitting parameter b is material dependent, thus the exponent of the atomic number varies.

The Jackson Hawkes method has proved accurate in determining the atomic number of elements, but this approach has limitations as it does not directly lead to quantitative information on the composition of the mixture under investigation. Additionally, the definition of only one effective atomic number, often called $Z_{eff}$, characterising a material is not valid over wide energy ranges or crucially for mixtures or assemblies containing elements with different atomic numbers. This gives inaccuracies when measuring compounds materials, and does not provide discrimination of compounds which may be engineered to look similar in this one property. This method does provide a useful approximation for some radiation studies, however the functionality is limited.

The detection and identification of concealed items inside bottles, packets, electronic devices etc is of key importance in the security industry. In addition the detection of non conforming products in the manufacturing industry are amongst many key areas where X-ray techniques can be used. The limitations of the above approaches are particularly applicable in such cases.

SUMMARY

In accordance with the invention in a first most complete aspect a method for monitoring objects for example for facilitating the identification and/or authentication of objects comprises:

in a first recording phase:

irradiating an object with a suitable source of radiation, collecting intensity information about radiation emergent from the object, resolving the intensity information spectroscopically between at least two energy bands, and storing the resultant dataset as a reference dataset; and in a second verification phase:

irradiating an object with a suitable source of radiation, collecting intensity information about radiation emergent from the object, resolving the intensity information spectroscopically between at least two energy bands, and using the resultant dataset as a test dataset;

identifying the object and retrieving its corresponding reference dataset; comparing the test dataset and the reference dataset within predetermined tolerance limits, and:

in the event that the reference dataset and the test dataset correspond within the predetermined tolerance limits, treating the object as verified or in the event that the reference dataset and the test dataset differ by more than the predetermined tolerance limits, in a third identification phase:

numerically processing the resolved intensity information from the test dataset to derive therefrom a dataset of information characteristic of the composition of the object, and using this information to identify the composition of the object.

BRIEF DESCRIPTION OF THE DRAWINGS

For a more complete understanding of the present invention and for further objects and advantages thereof, reference may now be had to the following description taken in conjunction with the accompanying drawings in which:

FIG. 1 is a flow diagram of a method for monitoring objects.

DETAILED DESCRIPTION

Thus, the principle of the invention is that of taking a reference dataset for an object which it is known will be required to be subsequently tested in an initial reference condition, to use this dataset to authenticate on subsequent testing that the object has not been changed from its initial reference condition, and only if the object has been changed from its initial reference condition to perform a more complete numerical processing step to identify the composition of the object as such. This is a potentially more powerful but more efficient process than either a simple verification against reference or a full numerical analysis performed alone on every test object.

Conveniently a reference database may be built up for multiple objects, for example which might need to be taken repeatedly through a security checkpoint, to provide a quick means of checking consistency with an initial reference condition or detection of unauthorised condition change.

The invention is suited to dual/multispectral techniques and systems where emergent intensity data is resolved spectroscopically between at least two energy bands and more preferably at least three energy bands simultaneously and/or successively. A data collection step preferably comprises resolving the intensity data items spectroscopically between at least two energy bands and more preferably at least three energy bands simultaneously and/or successively across the spectrum of the source. Dual/multispectral techniques give more detailed information on which the numerical processing step in particular can work to identify the composition of the object. In accordance with the invention emergent intensity data is resolved spectroscopically between at least two energy bands and more preferably at least three energy bands prior to the verification phase. This resolution is also used to give more detailed information on which the numerical processing step in particular can work to identify the composition of the object in the identification phase.

The radiation source preferably comprises one or more sources to deliver high-energy radiation such as ionizing radiation, for example high energy electromagnetic radiation such as X-rays and/or gamma rays, or subatomic particle radiation, and the detection system is adapted correspondingly to detect radiation in this spectrum. The radiation source for example is a broadband source such as a broadband X-ray or gamma-ray source capable of producing broad spectrum emission over a wide range of energies. Additionally or alternatively, multiple sources may be used to produce such a broad spectrum emission over a wide range of energies. The source(s) are such as to enable an object under test to be irradiated across a broad enough spectrum to facilitate the resolution of the emergent intensity data into plural intensity bins as required for the subsequent data processing steps.

The invention is applied to dual and/or multispectral techniques and systems where emergent intensity data is resolved spectroscopically between at least two energy bands and more preferably at least three energy bands simultaneously and/or successively.

In a possible embodiment, spatially resolved data is collected, for example in the form of an image dataset. Each data collection step preferably comprises resolving the intensity data items spatially for example to produce respectively a reference image dataset and a test image dataset.

The technique has particular uses in secure facilities such as military bases or government offices where all laptops and personal electronic equipment may be scanned into a database and ID tagged. These items can then be rescanned at entry and exit points. Other possible applications include open facilities such as airports where standard bar coded items such as cans and bottles can be added to a database.

In manufacturing industries this technique may be used in order to identify products which do not meet quality control limits e.g. missing components, incorrectly aligned components, spoiled food stuffs etc.

Each irradiation and data collection step may comprise:

providing a radiation test source of desired radiation and a detector system therefor spaced therefrom, the detector system being capable of detecting and collecting spectroscopically resolvable information about radiation from the source incident thereon;

causing radiation from the source to be incident upon the object, at least in the region of the marker material;

collecting intensity information about radiation received at the detector system after interaction with the object;

spectroscopically resolving the collected intensity information across a plurality of and preferably at least three energy bands within the spectrum of the source.

It will be understood that the overall methodology of the invention in the first complete aspect includes a reference phase comprising a recording phase and a test phase comprising a verification and where applicable an identification phase which are likely to be carried out remotely from each other in space and time and independently.

Accordingly, the invention in a further aspect comprises performance of the recording phase, for example on a large plurality of objects, to create a reference database.

Likewise in a further aspect the invention comprises performance of a test phase comprising the verification phase and where applicable thereafter the identification phases on a test object with reference to a previously generated reference database to authenticate that a test object remains in the reference condition and identify its contents or composition if it does not. By performing the test phase comprising the verification phase in all cases, and the identification phase where necessary on the same resolved data and hence potentially accessing data from the same previously generated reference database, efficiencies are obtained over either phase performed separately.

Outlined here by way of example is a method of identifying the differences in a scanned object from that of a database entry by using either a single X-ray measurement through a sample or by using an array of detectors in order to form a complete image.

The example considered here concerns the detection of an unexpected material within a portable DVD player. The procedure involves scanning the DVD player and storing the X-ray spectrum information for each point on the DVD player. This scan then becomes the database entry. As the detectors used in this specific example are multispectral detectors the X-ray intensity information can be gathered at a range of energies and is referred to here as $I(E)_{Database}$ for a given energy, E.

The DVD player can then be rescanned at any subsequent time and the new scan, $I(E)_{scan}$, compared to the database entry.

Due to the complexity of the scanned object it may not be immediately clear that a concealed threat is present. A numerical method of image comparison may be preferred.

A particular implementation uses the following normalisation in order to make the comparison between the scanned data and the database entry however other methods may be used.

$$I(E)_{Out} = I(E)_{Scan} / I(E)_{Database} \quad\quad 1.1$$

By normalisation against the database entry the difference can not only be made visible but can composition be identified using further numerical processing. In a preferred case a numerical method is used to generate data items calculated as representative of one or more orders of Compound Proton Number and/or an effective mass thickness and/or a density and not based on transmitted intensity alone. This technique may be used for example to process an image by layer removal, segmentation etc. In a particularly preferred case a Compound Proton Number Set as herein defined is used. A further dataset of data items representative of a mass thickness, may be included in the process to gather the Compound Proton Number Set.

Accordingly in a preferred case the dataset of information characteristic of the composition of the object comprises one or more orders of Compound Proton Number and/or an effective mass thickness and/or a density and in particular a Compound Proton Number Set and in particular preferably a Compound Proton Number Set as herein defined and the step of numerically processing the spectroscopically resolved intensity data comprises the following steps:

considering a material attenuation coefficient as a plural set of energy dependent polynomial equations with a set of energy dependent coefficients across the said plural set of energy bands;

determining a measured attenuation coefficient at each said energy band; calculating therefrom one or more orders of Compound Proton Number and/or an effective mass thickness and/or a density and in particular a Compound Proton Number Set;

making the one or more orders of Compound Proton Number and/or an effective mass thickness and/or a density and in the preferred case the Compound Proton Number Set available for the purposes of identifying the material content of the object.

Preferably the method comprises calculating at least two of: one or more orders of Compound Proton Number and/or effective mass thickness and/or density; and for example at least two orders of Compound Proton Number as a Compound Proton Number Set.

As has been defined herein, a Compound Proton Number Set comprises multiple orders of weighted compound atomic number. In their infinite form such numbers identify and depend upon the composition of a compound. The invention includes a method for calculating a number and preferably a high number of dimensions of the Compound Proton Number Set using X-ray measurements measured at multiple energies, as a method for material identification.

The invention in this embodiment comprises calculating one or more orders of Compound Proton Number and/or effective mass thickness and/or density and in the preferred case comprises calculating a Compound Proton Number Set as so defined, and making such data available for the purposes of identifying the material content of the object. Where use of such data is discussed herein, then except where the context necessarily requires otherwise the invention should be considered applicable to the use of one or more orders of Compound Proton Number and/or effective mass thickness and/or density in the general case and at least one Compound Proton Number Set as above defined in the preferred case.

The step of considering a material attenuation coefficient as a plural set of energy dependent polynomial equations comprises defining a numerical relationship comprising such a plural set of energy dependent polynomial equations with a set of energy dependent coefficients across the said plural set of energy bands, and for example making use of the formula of the general form:

$$\alpha(E)=a(E)+c(E)Z^2+d(E)Z^3 \ldots +y(E)Z^n$$

in particular for plural higher order powers and for example at least the second and third powers. Plural powers and in particular plural higher order powers of this general form are preferred. Although plural powers and in particular plural higher order powers of this general form are preferred the invention does not exclude making use of single orders of Z.

The step of numerically processing the spectroscopically resolved intensity data items to determine a further spatially resolved dataset of data items representative of a mass thickness, may be included in the process to gather the Compound Proton Number Set The preferred embodiment of the invention accepts the complexity of the attenuation inherent in multi-element compounds, and treats the attenuation coefficient as a set of energy dependent high order polynomial equations, with a set of energy dependent coefficients. As the number of energy levels is measured, higher orders of the atomic number can be included in the equation. If the coefficients can be measured accurately, these fits to plural powers and in particular higher order powers of atomic number (which have been called herein Compound Proton Numbers) can be calculated, and the Compound Proton Number Set created, from which the material may be identified. As is the case with fitting techniques, the accuracy of fitting increases with the number of independent measures. In the case of dual energy techniques, only two measurements across broad energy bands are available for fitting. The greater number of data points collections using multispectral detection methods thus increases the accuracy of this method.

With the absorption of elements a function of the atomic number, a single-value Compound Proton Number Set may be calculated for each element. Compounds of elements will have a higher-complexity attenuation dependent upon the higher order polynomials of weighted atomic number, and each compound will have a Compound Proton Number Set. If a solution for a range of powers (or orders) of Compound Proton Number is calculated, the value of Compound Proton Number will be different for each power (as is demonstrated later in equations 13-15), which is not the case for elements. The multiple fit parameters permitted by multispectral techniques allow the Compound Proton Numbers to be calculated for a range of orders, unlike for dual-energy techniques, thus providing greater knowledge of the whole Compound Proton Number Set thus better identification of the material.

In the preferred case of the invention, the method step of considering a material attenuation coefficient as a plural set of energy dependent polynomial equations with a set of energy dependent coefficients across the said plural set of energy bands comprises resolving at least two orders for the polynomial equations and for example at least two higher orders.

In the preferred case of the invention, the method step of calculating therefrom plural order powers of atomic number comprises calculating at least two higher order powers and for example at least the second and third powers.

The invention is applied to dual and/or multispectral techniques and systems where emergent intensity data is resolved spectroscopically between at least two energy bands and more preferably at least three energy bands simultaneously and/or successively.

The key to the preferred case of the invention is that collected intensity data is resolved spectroscopically between a plurality of energy bands across the incident spectrum, more preferably at least three, and more preferably a larger plurality. This resolution is used to determine one or more orders of Compound Proton Number and/or effective mass thickness and/or density and for example a Compound Proton Number Set as above described.

In order to effect this, a predetermined incident radiation spectrum is required across a breath of spectrum/range of energies broad enough to facilitate the resolution of the emergent intensity data into plural intensity bands as required for the subsequent data processing steps. Within this general requirement such energy bands may be broad or narrow to the point of tending to be single energies, and may be adjacent or be spaced apart, and may collectively encompass any part or all of the spectrum of one or more suitable sources.

It is not specifically pertinent to the invention how, by suitable combination of sources and detectors, such a spectroscopically resolved intensity dataset is generated.

One or more radiation sources may be used to generate a predetermined incident radiation spectrum of the desired breadth across the full breadth simultaneously or across parts thereof sequentially.

The resultant predetermined incident radiation spectrum of the desired breadth may be resolved into plural energy bands simultaneously for example in that the detector system preferably exhibits a spectroscopically variable response across at least a part of the source spectrum allowing spectroscopic information to be retrieved and allowing intensity information to be detected simultaneously at a plurality of, and for example at least three, differentiated energy bands across the spectrum of the source.

A detector system may be so adapted by provision of multiple detectors calibrated to different energies or by the provision of at least one detector adapted to produce spectroscopic resolution inherently in that it exhibits a direct spectroscopic response. In particular such a detector is fabricated from a material selected to exhibit inherently as a direct material property a direct variable electrical and for example photoelectric response to different parts of the source spectrum. Such a detector may be a dual energy detector adapted to distinguish between two energy levels within the incident spectrum, or may be a genuinely multispectral detector adapted to distinguish between three or more energy levels within the incident spectrum.

The principles may be combined to distinguish a larger plurality of energy bands. For example a detector system may be used comprising a plurality of detectors that exhibit a spectroscopically variable response across at least a part of the incident spectrum with such detectors additionally calibrated to different energies. In a specific case of such a concept plural dual energy detectors calibrated to different energies may be used in order to distinguish between more than two energy levels within the incident spectrum.

Additionally or alternatively the resultant predetermined incident radiation spectrum of the desired breadth may be resolved into plural energy bands sequentially, for example using multiple detectors sequentially and/or filters and/or cycling incident radiation frequency.

In the preferred case, a multispectral X-ray technique is employed in which emergent intensity data is resolved spectroscopically between at least three energy bands simultaneously. Access to a plurality of energy bins provides information which is inaccessible to a dual energy system in particular in resolving higher orders of Compound Proton Number. As noted, this may be effected by using plural dual energy detectors calibrated to different energies and/or by using one or more multispectral detectors adapted to distinguish between three or more energy levels within the incident spectrum Multispectral X-ray techniques whether using truly multispectral detectors, for example CdTe-type detectors, or using plural dual energy detectors calibrated to different energies, offer many advantages over traditional dual energy systems. For a dual energy system the two energy regions are not entirely discrete due to the non-zero probability of detection of high energy X-rays in the low energy detector and vice versa. In addition the cut off between high and low energy bins is not precise, resulting in an overlap between the two energy regions. The detectors used for such systems are generally scintillation detectors, which are typically operated in a current mode which records the product of the interaction rate and the charge per interaction. As such these systems do not provide a photon counting capability and instead simply give a measure of the total deposited energy. Scintillator response times are also quite slow, resulting in blurring of images and a loss of spatial resolution owing to afterglow effects.

In contrast a CdTe multispectral detector operates in pulse mode which preserves the energy and timing of individual events. The system is therefore capable of simultaneous measurement of the energy of each detected X-ray which can be measured to an accuracy fundamentally limited only by the detector resolution. As such systems use only a single detector to measure all energies each energy bin is discrete in nature with no overlapping between bins.

A suitable detector for implementation of the invention comprises one or more detector elements of a semiconductor material adapted for high energy physics applications, such as a material able to act as a detector for high energy radiation, and for example high energy electromagnetic radiation such as X-rays or gamma rays, or subatomic particle radiation. The resultant device comprises at least one layer of such material and is thus a device adapted for high energy physics applications, and for example a detector for high energy radiation such as X-rays or gamma rays, or subatomic particle radiation. The method comprises the use of such a device.

The semiconductor device is preferably a detector device adapted to exhibit a spectroscopically variable response across at least a substantial part of the intended radiation spectrum in use. In particular the semiconductor material is used that exhibits inherently as a direct material property a direct variable electrical and for example photoelectric response to different parts of the radiation spectrum in use.

In a preferred embodiment the semiconductor material is formed as a bulk crystal, and for example as a bulk single crystal (where bulk crystal in this context indicates a thickness of at least 500 µm, and preferably of at least 1 mm).

In a preferred embodiment the semiconductor material may be selected from Group II-VI semiconductors and in particular may be selected from cadmium telluride, cadmium zinc telluride (CZT), cadmium manganese telluride (CMT), and alloys thereof, and for example, save for incidental impurities, consists essentially of crystalline $Cd_{1-(a+b)}Mn_aZn_bTe$ where a+b<1 and a and/or b may be zero. A composite device may also have other detector elements of other materials for additional functionality.

The invention in the preferred embodiment involves resolving plural powers and especially plural higher order powers of atomic number (as referred to herein, a Compound Proton Number Set) and making this Compound Proton Number Set available for the purposes of identifying the material content of the object.

Measured data may be compared with library data for known materials. For example, the one or more orders of Compound Proton Number and/or an effective mass thickness and/or a density and for example the Compound Proton Number Set is made available for comparison against a database of datasets of one or more orders of Compound Proton Number and/or an effective mass thickness and/or a density and for example Compound Proton Number Set for a range of known materials and the method in the preferred embodiment comprises the step of comparing a measured Compound Proton Number Set against a library database of such known equivalent data.

In a preferred case for example the method may be applied to facilitate the detection of the presence of and/or classification or identification of particular target materials within a test object, for example materials which might represent a threat to security, a breach of customs regulations or the like.

In such a case, a library database comprising such data and for example at least Compound Proton Number Sets for a range of such threat materials is provided, and the comparison step comprises comparing measured and derived data and for example Compound Proton Number Sets for an object under test against such a database.

In accordance with the invention, radiation emergent from the test object is processed at least spectroscopically between a plural set of energy bands across the spectrum of the source. The invention does not preclude further processing and subdivision of the data, for example for the purposes of spatial resolution, depth resolution, for generation of imaging information, or for any other desired purpose.

In the preferred case, the step of collecting at the detector system intensity data for radiation emergent from the test object comprises at least the step of collecting transmitted intensity data, and for example comprises a step of collecting only transmitted intensity data, and the numerical processing steps comprise determining therefrom an attenuation coefficient related to attenuation of transmitted intensity.

In possible embodiment a numerical method is used to generate data items calculated as representative of one or more orders of Compound Proton Number and/or an effective mass thickness and/or a density and this data is used to process an image by layer removal. Such a method may be applied to radiological examination of an unknown object having plural layers of different materials composition including at least one layer of unknown composition, for example to detect a hidden layer of target, contraband or threat material In this embodiment the method comprises the particular steps of:

irradiating a test object and collecting at the detector system a dataset of intensity data from the radiation emergent from and for example transmitted through the test object;

resolving the intensity data items spectroscopically between at least two energy bands across the spectrum of the source;

determining from the spectroscopically resolved data items a further dataset of data items representative of one or more orders of Compound Proton Number and/or an effective mass thickness and/or a density, and most preferably a Compound Proton Number Set as above defined;

using the further dataset to generate deconvolved data for at least the layer of unknown composition and for example of each of the plural layers of different materials composition.

Thus, the Compound Proton Number Set so generated can be used, for example against reference data, to draw conclusions about the composition of the layer of unknown composition, for example to classify or identify it as a threat or contraband material.

It will be understood generally that each numerical step in the method of the invention can be implemented by a suitable set of machine readable instructions or code. These machine readable instructions may be loaded onto a general purpose computer, special purpose computer, or other programmable data processing apparatus to produce a means for implementing the functions specified.

These machine readable instructions may also be stored in a computer readable medium that can direct a computer or other programmable data processing apparatus to function in a particular manner, such that the instructions stored in a computer readable medium produce an article of manufacture including instruction means to implement some or all of the steps in the method of the invention. Computer program instructions may also be loaded onto a computer or other programmable apparatus to produce a machine capable of implementing a computer executed process such that the instructions are executed on the computer or other programmable apparatus providing steps for implementing some or all of the steps in the method of the invention. It will be understood that a step can be implemented by, and a means of the apparatus for performing such a step composed in, any suitable combinations of special purpose hardware and/or computer instructions In accordance with the invention in a further aspect there is provided at least one computer program comprising program instructions which when loaded onto a suitable computer will cause the computer to perform one or more and for example all of the numerical processing steps of the method of the first aspect of the invention.

The at least one computer program may without limitation be embodied on a computer-readable recording medium or read-only memory, stored in a memory of a computer, stored in a remote memory accessible by a computer for example via a distributed network, or carried on a suitable carrier signal.

An embodiment of a possible numerical analysis method in accordance with the invention for the generation of a Compound Proton Number Set will now be discussed by way of example only.

Expressed numerically, from the Compound Proton Number Set, we define the Compound Proton Number of order n as $_{CPN}{}^n Z$. A preferred Compound Proton Number Set comprises at least n=2, n=3.

One simple embodiment of the method which has been used for material identification is to use three energy bins, and using the following approximation for the mass attenuation coefficient for all elements:

$$\alpha(E) = a(E) + c(E)Z^2 + d(E)Z^3 \qquad 4$$

For a compound material the mass attenuation coefficient is given by the sum of the individual attenuation coefficients ($\alpha_i$) weighted by their mass fraction, $w_i$, so that $$\alpha_{compound} = \sum_i w_i \alpha_i \qquad 5$$

Therefore:

$$R(E) = \ln(I_0(E)/I(E)) = x \sum_j w_j (a(E) + c(E) Z_j^2 + d(E) Z_j^3) \qquad 6$$

where $w_j$ is the mass fraction of the element j within the material under investigation.

Rearranging Equation 6 gives:

$$R(E) = x \left[ a(E) \sum_j w_j + c(E) \sum_j w_j Z_j^2 + d(E) \sum_j w_j Z_j^3 \right] \qquad 7$$

So $$R(E) = x[a(E) + c(E)\overline{Z^2} + d(E)\overline{Z^3}] \qquad 8$$

where $\overline{Z^2}$ and $\overline{Z^3}$ are the simple weighted mean square and mean cube of the atomic number respectively. Here, the second order Compound Proton Number $$_{CPN}^2 Z = \sqrt[2]{(\overline{Z^2})}$$

and the third order Compound Proton Number $$_{CPN}^3 Z = \sqrt[3]{(\overline{Z^3})}$$

The components a(E), c(E) and d(E) can be found empirically either by experiment or by simulation in Geant4. This is done by carrying out I and $I_0$ measurements on a range of calibration items of known atomic mass and mass thickness. Equation 8 can then be solved for coefficients a(E), c(E) and d(E) across the energy bins.

The simplest way of doing this fit is to use just three energy bins, which we label 1, 2 and 3. To shorten the equations we define $R_{Energy\ Bin\ 1} = R_1$, $a_{Energy\ Bin\ 3} = a_3$, etc. Then we rewrite equation 8 for the three energy bins to get the simultaneous equations;

$$R_1 = x[a_1 + c_1 \overline{Z^2} + d_1 \overline{Z^3}]$$
$$R_2 = x[a_2 + c_2 \overline{Z^2} + d_2 \overline{Z^3}]$$
$$R_3 = x[a_3 + c_3 \overline{Z^2} + d_3 \overline{Z^3}] \qquad 9$$

This is a matrix equation. If we know the matrix $$M = \begin{pmatrix} a_1 & c_1 & d_1 \\ a_2 & c_2 & d_2 \\ a_3 & c_3 & d_3 \end{pmatrix} \qquad 10$$

then we can invert it and multiply $M^{-1}$ by three measured R values to get the vector $(x, x\overline{Z^2}, x\overline{Z^3})$ for the material sample. This allows us to obtain the second and third orders of the Compound Proton Number Set in this embodiment, along with the mass thickness, x. The matrix M depends only on our choice of energy bins. Once we have found M we can use it for any material as long as our starting assumption of equation 4 is valid.

It would be possible to find M by taking numbers from the NIST database for example. But in reality it is better to base it on our own measurements of materials of known composition. This way we can expect that the biases of our measurement system will be (at least partly) absorbed into the matrix and when we apply it to our own measurements of an unknown material the measurement biases will be reduced. We refer to measurement of M as calibration. Calibration is particularly simple if we use pure elements. We measure the absorption in, say, energy bin 1 of samples of three different elements of atomic numbers $Z_A$, $Z_B$, $Z_C$ and mass thicknesses $x_A$, $x_B$ and $x_C$. The result is three simultaneous equations again $$R_1(Z_A)/x_A = a_1 + c_1 Z_A^2 + d_1 Z_A^3$$

$$R_1(Z_B)/x_b = a_1 + c_1 Z_B^2 + d_1 Z_B^3$$

$$R_1(Z_C)/x_C = a_1 + c_1 Z_C^2 + d_1 Z_C^3 \qquad 11$$

So once again we solve for $(a_1, c_1, d_1)$ by multiplying the vector of measured R/x values by $X^{-1}$, where $$X = \begin{pmatrix} 1 & Z_A^2 & Z_A^3 \\ 1 & Z_B^2 & Z_B^3 \\ 1 & Z_C^2 & Z_C^3 \end{pmatrix} \qquad 12$$

And repeat for the other two energy bins to get the whole of matrix M.

The calibration elements can be any elements covering the range of atomic numbers likely to be encountered in the analysis e.g. carbon, aluminium and copper as these cover the range of atomic numbers expected in a test object. The use of such an analysis method shows the potential for more advanced techniques than straightforward matching of spectra.

As a simple example to show how the second and third order Compound Proton Numbers will be different in a compound, but be the same in an element, consider a compound made up of two items in an atomic number of 2, and a second with an atomic number of 5, with a 50:50 combination by weight. Therefore, the second order Compound Proton Number $$_{CPN}^2 Z = \sqrt[2]{\left(\frac{1}{2} 2^2\right) + \left(\frac{1}{2} 5^2\right)} = 3.81 \qquad 13$$

And for the third order Compound Proton Number $$_{CPN}^3 Z = \sqrt[3]{\left(\frac{1}{2} 2^3\right) + \left(\frac{1}{2} 5^3\right)} = 4.05 \qquad 14$$

However for a single element of atomic number 5 both second and third order Compound Proton Numbers are identical (as indeed are any orders of Compound Proton Number).

$$_{CPN}^2 Z = \sqrt[2]{(5^2)} = 5 = \sqrt[3]{(5^3)} = {_{CPN}^3 Z} \qquad 15$$

As each material will have a different set of Compound Proton Numbers, the greater the dimensions of the Compound Proton Number that can be calculated the more information about the material can be gathered, and the material better identified. Further orders will readily be derivable using the same basic principles of the invention and sufficient plural energy bins of radiation data.

As an example measured on real apparatus, the calculation of mass thickness and the ability to measure both $_{CPN}^2 Z$ and $_{CPN}^3 Z$ can be exploited in order to distinguish powdered aluminium from a solid aluminium block. The oxide content is significantly greater in powdered aluminium due to the increased surface area over that of a solid block of aluminium. This then results in a compound which can be identified by the difference between the $_{CPN}^2 Z$ and $_{CPN}^3 Z$. Additionally, with the aid of a tomographic thickness measurement, the density of the material can be derived by dividing the mass thickness by the measured thickness. Densities deviating significantly from that of a solid block of aluminium are clearly powders.

Table 1 shows the resulting density, $_{CPN}^2 Z$ and $_{CPN}^3 Z$. The $_{CPN}^2 Z$ and $_{CPN}^3 Z$ are identical for the aluminium block and the density is over 95% of that expected for a solid block. In contrast the powdered aluminium shows a variation in $_{CPN}^2 Z$ and $_{CPN}^3 Z$ indicating the sample is a compound rather than a single element and the densities of both powder samples are significantly lower than expected for a solid block of material.

TABLE 1

Second and third order Compound Proton Numbers, $_{CPN}^2 Z$ and $_{CPN}^3 Z$, measured for aluminium powder and an aluminium block. The density was derived here from knowledge of the physical thickness of the samples and measurement of the mass thickness.

| Material | Mass thickness (gcm$^{-2}$) | Thickness (cm) | Density (gcm$^{-3}$) | $_{CPN}^2 Z$ | $_{CPN}^3 Z$ | % of Expected Density |
|---|---|---|---|---|---|---|
| Al powder in an aluminium can | 3.08 | 6.5 | 0.47 | 12.71 | 11.65 | 17.55 |
| Al block 1.56 cm | 4.02 | 1.56 | 2.58 | 12.92 | 12.92 | 95.46 |

FIG. 1 is a flow diagram illustrating a process 100 for monitoring objects. The process begins at step 102. At step 104, a reference object is irradiated with a suitable source of radiation. Intensity information about radiation emergent from the reference object is collected. The intensity information is resolved and stored as a reference dataset. At step 106, step 104 is repeated for a plurality of test objects thereby creating a reference database corresponding to the plurality of reference objects. At step 108, a test object is irradiated with the suitable source of radiation. Intensity information about radiation emergent from the test object is collected. The intensity information is resolved and stored as a test dataset. At step 110, the test object is identified and a corresponding reference dataset is retrieved from the reference database. At step 112, the test dataset is compared to the corresponding reference dataset. At step 114, it is determined if the test dataset and the reference dataset correspond with tolerance limits. If it is determined at step 114 that the test dataset and the reference dataset do correspond within tolerance limits, the process 100 proceeds to step 116. At step 116, the test object is treated as verified. If it is determined at step 114 that the test dataset and the reference dataset do no correspond within tolerance limits, the process 100 proceeds to step 118. At step 118, intensity information from the test dataset is numerically processed to derive a third dataset of information characteristic of a composition of the test object. The third dataset of information is utilized to identify the composition of the test object. The process 100 ends at step 120.

The invention claimed is:

1. A method for monitoring objects, the method comprising:
in a first phase:
irradiating a reference object with a suitable source of radiation, collecting intensity information about radiation emergent from the reference object, resolving the intensity information spectroscopically between at least two energy bands, and storing the resultant spectroscopically resolved intensity dataset as a reference dataset representing a reference condition for the reference object;
repeating the irradiating for a plurality of reference objects to create a reference database corresponding to the plurality of reference objects; and
in a second phase, performed independently:
irradiating a test object with the suitable source of radiation, collecting intensity information about radiation emergent from the test object, resolving the intensity information spectroscopically between at least two energy bands, and using the resultant spectroscopically resolved intensity dataset as a test dataset representing a test condition for the test object;
identifying the test object and retrieving a reference dataset from the reference database, the reference dataset corresponding to the test object;
comparing the test dataset and the reference dataset within predetermined tolerance limits to determine whether a test object remains in the reference condition, and
in the event that the reference dataset and the test dataset correspond within the predetermined tolerance limits, treating the test object as verified or
in the event that the reference dataset and the test dataset differ by more than the predetermined tolerance limits, in a third phase: and
numerically processing the resolved intensity information from the test dataset to derive therefrom a third dataset of information characteristic of the composition of the test object, and using this information to identify the composition of the test object.

2. The method in accordance with claim 1 wherein the step of numerically processing the spectroscopically resolved intensity data comprises:
numerically processing the resolved intensity information from the test dataset to derive therefrom at least one of one or more orders of Compound Proton Number, an effective mass thickness, and a density; and
making at least one of the one or more orders of Compound Proton Number, the effective mass thickness, and the density available for the purposes of identifying the material content of the test object.

3. The method in accordance with claim 2 wherein the step of numerically processing the spectroscopically resolved intensity data comprises:
considering a material attenuation as a plural set of energy dependent polynomial equations with a set of energy dependent coefficients across the said plural set of energy bands;
determining a measured attenuation coefficient at each said energy band;
calculating therefrom at least one of one or more orders of Compound Proton Number, an effective mass thickness, and a density, the one or more orders of Compound Proton Number being solutions to the plural set of energy dependent polynomial equations; and
making at least one of the one or more orders of Compound Proton Number, the effective mass thickness, and the density available for the purposes of identifying the material content of the test object.

4. The method in accordance with claim 3 wherein the step of numerically processing the spectroscopically resolved intensity data comprises:
considering a material attenuation coefficient as a plural set of energy dependent polynomial equations with a set of energy dependent coefficients across the said plural set of energy bands;
determining a measured attenuation at each said energy band;
calculating therefrom a Compound Proton Number Set, the Compound Proton Number Set being solutions to the plural set of energy dependent polynomial equations; and
making the Compound Proton Number Set available for the purposes of identifying the material content of the test object.

5. The method in accordance with claim 2 wherein the method step of considering a material attenuation coefficient as a plural set of energy dependent polynomial equations with a set of energy dependent coefficients across the said plural set of energy bands comprises resolving at least two orders for the polynomial equations.

6. The method in accordance with claim 2 wherein the method step of considering a material attenuation coefficient as a plural set of energy dependent polynomial equations with a set of energy dependent coefficients across the said plural set of energy bands comprises defining a numerical relationship comprising such a plural set of energy dependent polynomial equations with a set of energy dependent coefficients across the said plural set of energy bands.

7. The method in accordance with claim 6 making use of the formula of the general form:

$$\alpha(E)=a(E)+c(E)Z^2+d(E)Z^3 \ldots +y(E)Z^n.$$

8. The method in accordance with claim 3 comprising resolving at least two higher orders for the polynomial equations.

9. The method in accordance with claim 2 wherein the step of numerically processing the spectroscopically resolved intensity data items to determine an effective mass thickness comprises calculating the mass thickness alongside the Compound Proton Number Set.

10. The method in accordance with claim 2 wherein at least one of the one or more orders of Compound Proton Number, the effective mass thickness, and the density and for example the Compound Proton Number Set is made available for comparison against a database of datasets of at least one of the one or more orders of Compound Proton Number, the an effective mass thickness, and the density and for example Compound Proton Number Set for a range of known materials.

11. The method in accordance with claim 2 comprising the step of comparing measured data against a library database of known data for a range of known materials.

12. The method in accordance with claim 11 comprising providing a library database of known Compound Proton Number Sets for a range of particular target materials and comparing measured and derived Compound Proton Number Sets for the test object against such a database.

13. The method in accordance with claim 1 wherein the step of collecting at the detector system intensity data for radiation emergent from the test object comprises the step of collecting transmitted intensity data, and the numerical processing steps comprise determining therefrom an attenuation coefficient related to attenuation of transmitted intensity.

14. The method in accordance with claim 1 comprising the particular steps of:
- irradiating the test object and collecting at the detector system a dataset of intensity data from the radiation emergent from and for example transmitted through the test object;
- resolving the intensity data items spectroscopically between at least two energy bands across the spectrum of the source;
- determining from the spectroscopically resolved data items a further dataset of data items representative of at least one of one or more orders of Compound Proton Number, an effective mass thickness, and a density, and most preferably a Compound Proton Number Set; and
- using the further dataset to generate deconvolved data for at least the layer of unknown composition and for example of each of the plural layers of different materials composition.

15. The method in accordance with claim 1 wherein the source is an X-ray source, and the detection system is adapted correspondingly to detect and resolve X-rays between a plural set of energy bands.

16. The method in accordance with claim 1 wherein a detector system is provided that exhibits a spectroscopically variable response across at least a part of the incident spectrum allowing spectroscopic information to be retrieved and allowing intensity information to be detected simultaneously at a plurality of differentiated energy bands.

17. The method in accordance with claim 1 wherein emergent intensity data is resolved spectroscopically between at least three energy bands simultaneously.

18. A computer program product comprising a non-transitory computer-usable medium having computer-readable program code embodied therein, the computer-readable program code adapted to be executed to implement the method of claim 1.

* * * * *